(12) United States Patent
Contiliano et al.

(10) Patent No.: US 7,708,767 B2
(45) Date of Patent: *May 4, 2010

(54) POLYMER-BASED ORTHOPEDIC SCREW AND DRIVER SYSTEM WITH INCREASED INSERTION TORQUE TOLERANCE AND ASSOCIATED METHOD FOR MAKING AND USING SAME

(75) Inventors: Joseph H. Contiliano, Stewartsville, NJ (US); J. Jenny Yuan, Neshanic Station, NJ (US); Kevor S. Tenhuisen, Clinton, NJ (US)

(73) Assignee: Ethicon, Inc., Somerville, NJ (US)

( * ) Notice: Subject to any disclaimer, the term of this patent is extended or adjusted under 35 U.S.C. 154(b) by 262 days.

This patent is subject to a terminal disclaimer.

(21) Appl. No.: 11/133,013

(22) Filed: May 19, 2005

(65) Prior Publication Data

US 2005/0216016 A1    Sep. 29, 2005

Related U.S. Application Data

(63) Continuation of application No. 10/033,543, filed on Dec. 27, 2001, now Pat. No. 6,921,402.

(51) Int. Cl.
*A61B 17/04* (2006.01)

(52) U.S. Cl. ............... 606/916; 606/309; 606/104

(58) Field of Classification Search ............... 606/73, 606/916, 309, 331, 104, 321, 299, 77
See application file for complete search history.

(56) References Cited

U.S. PATENT DOCUMENTS

| | | | |
|---|---|---|---|
| 4,105,034 A | 8/1978 | Shalaby et al. | |
| 4,130,639 A | 12/1978 | Shalaby et al. | |
| 4,141,087 A | 2/1979 | Shalaby et al. | |
| 4,205,399 A | 6/1980 | Shalaby et al. | |
| 4,519,713 A | 5/1985 | Godsey et al. | |
| 4,537,185 A | 8/1985 | Stednitz | |
| 4,539,981 A * | 9/1985 | Tunc | 606/77 |
| 4,759,110 A * | 7/1988 | Rieger et al. | 29/447 |
| 4,927,421 A | 5/1990 | Goble et al. | |

(Continued)

FOREIGN PATENT DOCUMENTS

| | | |
|---|---|---|
| EP | 0 390 613 A1 | 8/1994 |
| EP | 0 471 334 B1 | 6/1997 |
| EP | 0 502 698 A1 | 11/1997 |
| EP | 0 913 131 A2 | 5/1999 |
| EP | 0 916 312 A1 | 5/1999 |

(Continued)

OTHER PUBLICATIONS

Allcock, H.R., et al., "Poly(phenylene Ether) to Radical Polymerization", Encyclopedia of Polymer Science and Engineering, John Wiley & Sons, Inc., vol. 13, 1988, pp. 31-41.

(Continued)

*Primary Examiner*—Pedro Philogene

(57) ABSTRACT

An orthopedic screw with an internal bore and mating driver has a bioabsorbable polymer component. To increase the torque tolerance of the screw and to minimize the likelihood of the driver stripping inside the bore of the screw, the screw and driver are heat treated together to shrink fit the screw onto the driver thereby increasing the driver-to-screw contact and distributing the loading force over a greater area to protect against material failure. The heat treatment involves heating the screw to an elevated temperature and holding that temperature for a period to promote stress relaxation and/or crystallization of the material.

22 Claims, 2 Drawing Sheets

U.S. PATENT DOCUMENTS

| | | | |
|---|---|---|---|
| 4,950,270 A | | 8/1990 | Bowman et al. |
| 5,030,048 A | * | 7/1991 | Massa ........................ 409/234 |
| 5,057,110 A | | 10/1991 | Kranz et al. |
| 5,062,843 A | | 11/1991 | Mahony, III |
| 5,152,790 A | | 10/1992 | Rosenberg et al. |
| 5,156,616 A | | 10/1992 | Meadows et al. |
| 5,169,400 A | * | 12/1992 | Muhling et al. ............... 606/73 |
| 5,348,026 A | | 9/1994 | Davidson |
| 5,364,400 A | | 11/1994 | Rego, Jr. et al. |
| 5,370,662 A | | 12/1994 | Stone et al. |
| 5,443,482 A | | 8/1995 | Stone et al. |
| 5,464,929 A | | 11/1995 | Bezwada et al. |
| 5,470,334 A | * | 11/1995 | Ross et al. ................... 606/916 |
| 5,522,817 A | | 6/1996 | Sander et al. |
| 5,529,736 A | | 6/1996 | Shalaby et al. |
| 5,571,139 A | | 11/1996 | Jenkins, Jr. |
| 5,584,836 A | | 12/1996 | Ballintyn et al. |
| 5,597,579 A | | 1/1997 | Bezwada et al. |
| 5,618,552 A | | 4/1997 | Bezwada et al. |
| 5,632,748 A | | 5/1997 | Beck, Jr. et al. |
| 5,645,547 A | | 7/1997 | Coleman |
| 5,645,850 A | | 7/1997 | Bezwada et al. |
| 5,695,497 A | | 12/1997 | Stahelin |
| 5,698,213 A | | 12/1997 | Jamiolkowski et al. |
| 5,711,669 A | | 1/1998 | Hurson |
| 5,743,914 A | | 4/1998 | Skiba |
| 5,810,821 A | | 9/1998 | Vandewalle |
| 5,824,011 A | | 10/1998 | Stone et al. |
| 5,824,247 A | | 10/1998 | Tunc |
| 5,827,287 A | * | 10/1998 | Tunc ............................ 606/76 |
| 5,859,150 A | | 1/1999 | Jamiolkowski et al. |
| 5,928,236 A | | 7/1999 | Augagneur et al. |
| 5,964,783 A | | 10/1999 | Grafton et al. |
| 5,968,045 A | | 10/1999 | Frazier |
| 6,001,101 A | | 12/1999 | Augagneur et al. |
| 6,022,352 A | | 2/2000 | Vandewalle |
| 6,096,060 A | | 8/2000 | Fitts et al. |
| 6,099,529 A | | 8/2000 | Gertzman et al. |
| 6,162,225 A | | 12/2000 | Gertzman et al. |
| 6,187,008 B1 | | 2/2001 | Hamman |
| 6,352,232 B1 | | 3/2002 | Yorwarth |
| 6,423,062 B2 | | 7/2002 | Enayati |
| 6,458,134 B1 | | 10/2002 | Songer et al. |
| 6,471,707 B1 | | 10/2002 | Miller et al. |
| 6,517,543 B1 | | 2/2003 | Berrevoets et al. |
| 6,519,828 B1 | | 2/2003 | Cook et al. |
| 6,547,792 B1 | | 4/2003 | Tsuji et al. |
| 6,565,291 B2 | | 5/2003 | Harpaz et al. |
| 6,605,090 B1 | * | 8/2003 | Trieu et al. ................... 606/281 |
| 6,916,321 B2 | | 7/2005 | TenHuisen et al. |
| 6,921,402 B2 | * | 7/2005 | Contiliano et al. ............ 606/73 |
| 2001/0034520 A1 | | 10/2001 | Enayati |
| 2003/0125749 A1 | | 7/2003 | Yuan et al. |

FOREIGN PATENT DOCUMENTS

| | | |
|---|---|---|
| EP | 1 055 398 A1 | 11/2000 |
| FR | 2 270 627 A1 | 12/1995 |
| FR | 2 271 819 A1 | 1/1996 |
| JP | 07 213534 A1 | 8/1995 |
| JP | 11 70126 A1 | 3/1999 |
| WO | WO 93/15682 A1 | 8/1993 |
| WO | WO 94/07425 A1 | 4/1994 |
| WO | WO 95/18577 A1 | 7/1995 |
| WO | WO 96/09014 A1 | 3/1996 |
| WO | WO 96/25104 A1 | 8/1996 |
| WO | WO 97/46167 A1 | 12/1997 |
| WO | WO 99/11177 A2 | 3/1999 |
| WO | WO 00/23424 A1 | 5/2000 |
| WO | WO 2005/9389 A1 | 10/2000 |

OTHER PUBLICATIONS

Cohn, D. et al., "Biodegradable PEO/PLA Block Copolymers", Journal of Biomedical Materials Research, vol. 22, John Wiley & Sons, Inc., 1988, pp. 993-1009.

Cohn, D., "New Tailor-made Biodegradable Polymeric Biomaterials", Polymer Preprints, vol. 30, The Division of Polymer Chemistry, Inc., Apr. 1989, p. 498.

Feagin, Jr., J.A. (ed.), "Diagnosis and Treatment of Ligamentous Injuries About the Knee", The Crucial Ligaments, Churchill Livingstone, Inc., New York, 1988, pp. 179-195 and 401-408.

Fu, F.H. et al., "Current Trends in Anterior Cruciate Ligament Reconstruction, Part I: Biology and Biomechanics of Reconstruction", The American Journal of Sports Medicine, vol. 27, No. 6, American Orthopaedic Society for Sports Medicine, 1999, pp. 821-830.

Fu, F.H. et al., "Current Trends in Anterior Cruciate Ligament Reconstruction, Part II: Operative Procedures and Clinical Correlations", The American Journal of Sports Medicine, vol. 28, No. 1, American Orthopaedic Society for Sports Medicine, 2000, pp. 124-130.

Heller, J., "Poly (Ortho Esters)", Handbook of Biodegradable Polymers, Hardwood Academic Publishers, 1997, pp. 99-118.

Kemnitzer, J. And Kohn, J., "Degradable Polymers Derived from the Amino Acid L-Tyrosine", Handbook of Biodegradable Polymers, Hardwood Academic Publishers, 1997, pp. 251-272.

Rosen, V. and Theis, R.S., The Cellular and Molecular Basis of Bone Formation and Repair, R.G. Landes Company, Texas, 1995, pp. 1-41.

Vandorpe, J. et al., "Biodegradable Polyphosphazenes for Biodmedical Applications", Handbook of Biodegradable Polymers, Harwood Academic Publishers, 1997, pp. 161-182.

Amendment After Final Rejection, dated Jan. 19, 2005, in response to Office Action dated Oct. 22, 2004, received in U.S. Appl. No. 10/033,543, filed on Dec. 27, 2001.

Office Action dated Oct. 22, 2004, received in U.S. Appl. No. 10/033,543, filed on Dec. 27, 2001.

Amendment, dated Jul. 22, 2004, in response to Office Action dated Jul. 22, 2004, received in U.S. Appl. No. 10/033,543, filed on Dec. 27, 2001.

Office Action dated Mar. 22, 2004, received in U.S. Appl. No. 10/033,543, filed on Dec. 27, 2001.

Amendment, dated Feb. 17, 2004, in response to Office Action dated Feb. 17, 2004, received in U.S. Appl. No. 10/033,543, filed on Dec. 27, 2001.

Office Action dated Oct. 16, 2003, received in U.S. Appl. No. 10/033,543, filed on Dec. 27, 2001.

Amendment, dated Aug. 8, 2003, in response to Office Action dated May 12, 2003, received in U.S. Appl. No. 10/033,543, filed on Dec. 27, 2001.

Office Action dated May 12, 2003, received in U.S. Appl. No. 10/033,543, filed on Dec. 27, 2001.

* cited by examiner

POLYMER-BASED ORTHOPEDIC SCREW AND DRIVER SYSTEM WITH INCREASED INSERTION TORQUE TOLERANCE AND ASSOCIATED METHOD FOR MAKING AND USING SAME

CROSS-REFERENCE TO RELATED APPLICATION

The present application is a continuation of U.S. patent application Ser. No. 10/033,543, filed on Dec. 27, 2001 now U.S. Pat. No. 6,921,402.

FIELD OF THE INVENTION

The present invention relates to orthopedic screws and screw drivers and more particularly to cannulated screws and screws with an internal bore having a polymer component and methods for making and using same.

BACKGROUND OF THE INVENTION

Medical screws of various designs and material composition are used to affix medical implants, grafts and bone fragments to substrate bone structures during orthopedic surgery. One surgical use involves insertion of an interference screw into a bone tunnel to secure an end of an anterior cruciate ligament (ACL) replacement graft in place. ACL reconstruction procedures and interference screws are disclosed, e.g., in U.S. Pat. Nos. 5,062,843, 4,950,270 and 4,927,421.

Medical screws have typically been fabricated from medically approved metallic materials, such as stainless steel or titanium, which are not absorbed by the body. Screws made of these strong materials exhibit sufficient torsional strength to withstand the torque necessary to insert the screw into bone. A disadvantage of such screws, however, is that once healing is complete, an additional surgical procedure may be required to remove the screw from the patient. Metallic screws may include a threaded shank joined to an enlarged head having a transverse slot or hexagonal socket formed therein to engage, respectively, a similarly configured, single blade or hexagonal rotatable driver for turning the screw into the bone. The enlarged heads on such screws can protrude from the bone tunnel and can cause chronic irritation and inflammation of surrounding body tissue.

Permanent metallic medical screws in movable joints can, in certain instances, cause abrading of ligaments during normal motion of the joint. Metallic screws also occasionally back out after insertion, protruding into surrounding tissue and causing discomfort. Furthermore, permanent metallic screws and fixation devices may shield the bone from beneficial stresses after healing. It has been shown that moderate periodic stress on bone tissue, such as the stress produced by exercise, helps to prevent decalcification of the bone. Under some conditions, the stress shielding which results from the long term use of metal bone fixation devices can lead to osteoporosis.

Biodegradable or bioabsorbable interference screws have been proposed to avoid the necessity of surgical removal after healing. Because the degradation of a biodegradable screw occurs over a period of time, support load is transferred gradually to the bone as it heals. This reduces potential stress shielding effects. Conventional bioabsorbable interference screws commonly have a polymer component and are softer and weaker than metallic screws, such that they are not self-tapping, requiring the hole drilled into the bone to receive the screw to be tapped (threaded). The necessity to tap holes in the injured bone adds to the complexity of the surgical procedure and lengthens the time required to complete the operation.

In addition, screws having a polymer component, hereinafter referred to as "polymer screws" exhibit substantially lower torsional strength than conventional metal screws, making them susceptible to deformation when subjected to the torsional loads required to drive the screw into relatively hard tissue such as bone. The high torque that must be applied to medical screws by a driver can cause shear deformation of the relatively soft polymeric material, causing damage to the screw, e.g., the driver can "strip" the recess or slot provided on the screw for the driver. If the screw is not inserted in bone to the proper depth at the point of the failure, difficulty may arise in driving the screw further in, or backing the screw out.

A number of approaches have been used to alleviate the shear deformation of polymer medical screws including low friction coatings, internal reinforcement with fibers or composite formations, crystalline orientation via subjection to compression and screw head design. In yet another approach, as shown in U.S. Pat. No. 5,169,400 (to Muhling, et al.), U.S. Pat. No. 5,470,334 and EP 0502698A1 (to Ross, et al.), and U.S. Pat. No. 5,695,497 (to Stahelin, et al.), a central cannula or recess having a non-circular cross-section running a portion of or the entire length of the screw is provided. The noncircular cross-section is disclosed as being of various shapes (hexagonal, square, star-shaped, etc. in cross-section, or with a plurality of radial force or lobe members) with a complementarily shaped screwdriver bit to increase torque transfer. Manufacturing tolerances for forming the cannula/bore of the screw and its mating bit limit the amount of surface-to-surface contact between the cannula/bore and bit. Decreased surface-to-surface contact may result in higher stresses and an increased risk of torque failure.

This limitation is not overcome by the approach shown in U.S. Pat. No. 5,584,836 (to Ballintyn, et al.), of using a plurality of cannulae. Multiple cannula and mating driver projections are weaker than a single projection, add manufacturing complexity, and are still subject to manufacturing tolerances. This is especially an issue when complicated geometries are employed. Greater surface-to-surface contact at the driver/screw cannula interface distributes the forces exerted on the screw by the driver, reducing localized stresses and enabling a higher torque to be applied to the driver before the strength limit of the screw material is reached. Efforts to reduce manufacturing tolerances on mating parts can be cost prohibitive and time consuming to both manufacture and inspect.

Accordingly, it would be advantageous to provide a polymeric-based, cannulated medical screw or medical screw with a tool receiving bore and associated driver, wherein the outer surface of the driver and the cannula/bore surface are closely mated to increase the insertion torque tolerance of the screw.

SUMMARY OF THE INVENTION

The limitation of prior art orthopedic screw and driver systems are remedied by the present invention which includes an elongated screw having external threads and an internal bore extending through the screw at least a portion of its length. The screw is made at least partially of a bioabsorbable material. The system includes an elongated driver having a non-circular cross-sectional shape approximating the cross-sectional shape of the screw bore. The driver is insertable into the bore and is matingly received therein to transfer rotational motion of the driver to the screw. The bore exhibits a closely mating shrink-fit relative to the driver.

A method of the present invention for increasing driver-to-screw contact includes the steps of inserting the driver into the bore of the screw; heating the screw; and allowing the screw to cool. The steps of heating and cooling inducing the screw to shrink, whereby the bore exhibits a closely mating shrink-fit relative to the driver.

DETAILED DESCRIPTION OF THE INVENTION

Figure 1:
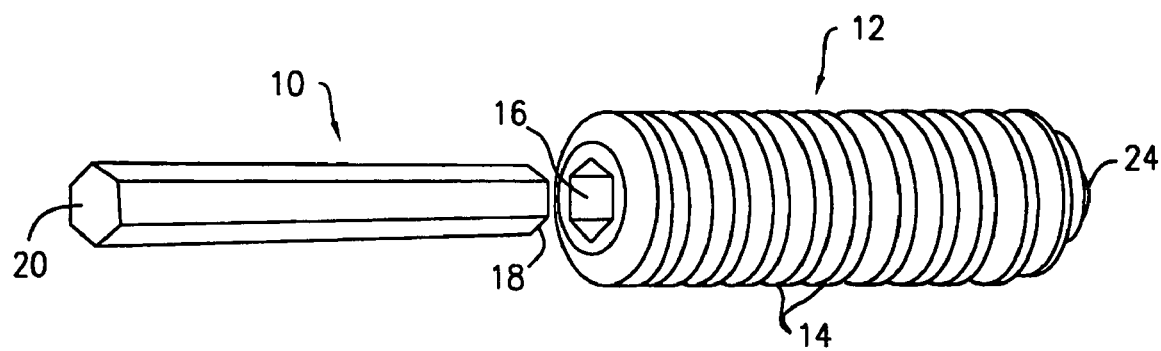
FIG. 1 is a perspective view of a driver and screw combination in accordance with an embodiment of the present invention.

The present invention relates to an orthopedic screw and driver system and method for making and using same. A polymeric-based cannulated medical screw or a screw with a tool-receiving bore is placed on a driver with the driver extending into the cannula/bore. The assembly is then subjected to a heat treatment process wherein the cannula/bore of the screw shrinks and molds itself to the driver, thus creating a mating interface both longitudinally and circumferentially thus minimizing dimensional variations between mating parts. The screw is driven into the selected substrate and the driver removed from the cannula/bore thereof. The mating of the driver to the screw cannula/bore increases the insertion torque tolerance of the screw. The present invention, therefore, allows cannulated screws or screws with tool bores composed mainly of bioabsorbable, polymeric materials to be inserted into bone with a decreased risk of shear deformation of the screw caused by the torque required to drive the screw into bone.

Referring to FIGS. 1 through 4, driver 10 is an elongated, generally hexagonal tool used for turning screw 12. Screw 12 is generally cylindrical in shape and has a plurality of external threads 14, a subset of which are lead-in or starter threads $14_L$ that assist the screw 12 in threading into a pilot hole drilled in the substrate, e.g., bone. The screw 12 may also be conically tapered toward the tip 24 to aid in its introduction into a substrate. While the taper shown extends only a short distance from the tip 24, a longer taper may be employed, e.g., extending half or the entire length of the screw 12, with the angle and length of taper depending upon the application. The screw 12 has an axial bore 16 which is generally hexagonal in shape to matingly receive the driver 10 therein. The bore 16 does not extend through the entire length of the screw 12. Alternatively, the bore 16 may extend through the entire length of the screw 12. The driver 10 and bore 16 may be other shapes, including, but not limited to, polygonal, cross, star, or oval shapes. Driver 10 is preferably tapered down from the proximal end 20 to the distal end 18 for easier removal of the driver 10 from the screw 12 after it is inserted into a substrate. Proximal end 20 of driver 10 may be received in a chuck or snap-fit recess of a handle, wrench or electric power tool (now shown) to facilitate turning the screw 12. A short driver 10 is depicted for ease of illustration, but any length may be employed to provide proper access to the insertion site.

Figure 2:
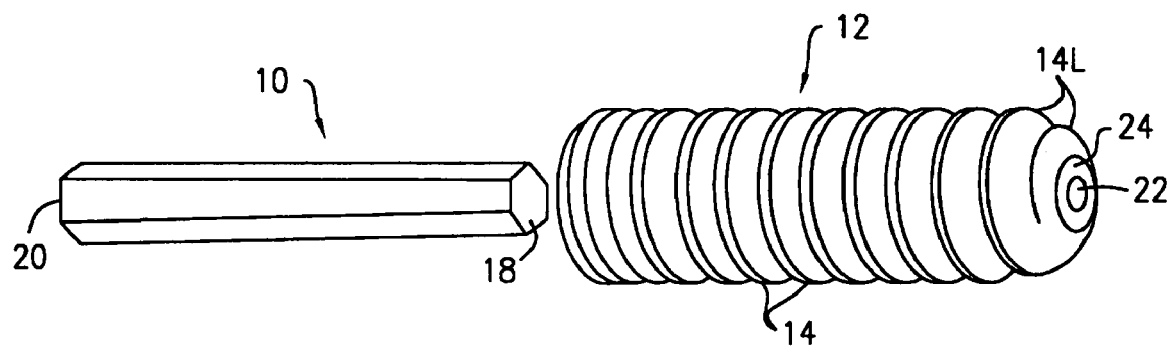
FIG. 2 is another perspective view of the driver and screw combination of FIG. 1.
Figure 3:
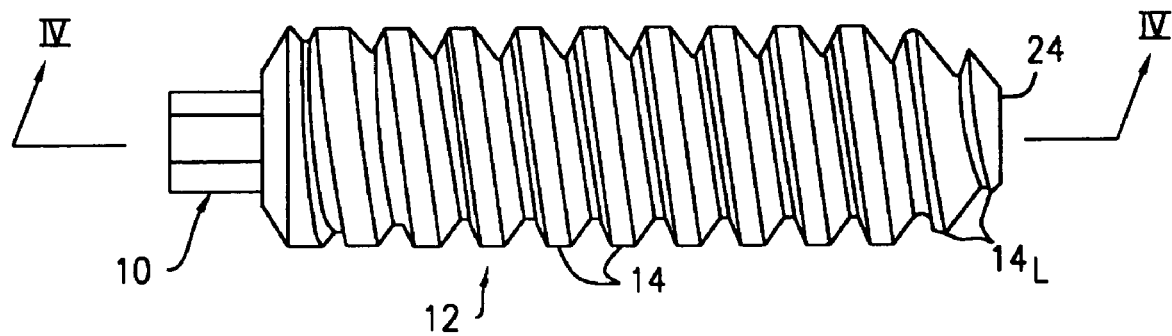
FIG. 3 is an elevational view of the driver and screw combination of FIGS. 1 and 2 with the driver inserted into the screw.
Figure 4:
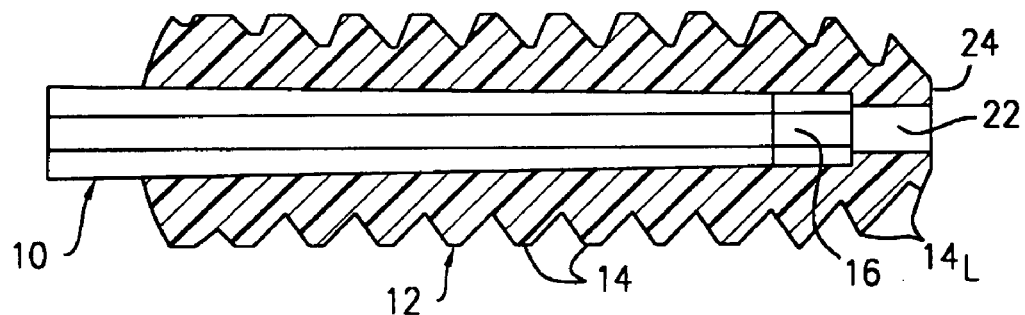
FIG. 4 is a partially cross-sectional view of the driver and screw of FIG. 3 taken along section line IV-IV and looking in the direction of the arrows.
Figure 5:
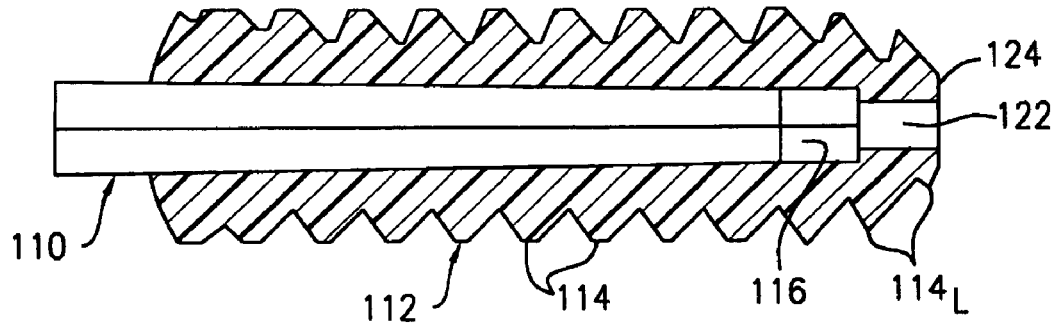
FIG. 5 is a partially cross-sectional view like that of FIG. 4, but of an alternative embodiment of the present invention.

As shown in FIGS. 2 and 4, the screw 12 may have a guide wire cannula 22 through which a guide wire (not shown) may be inserted for the purpose of guiding the screw 12 into position, e.g., during arthroscopic surgery. In a similar manner, the driver 10 may be cannulated for the placement of a guide wire therethrough. As shown in FIG. 4, the bore 16 extends almost the entire length of the screw 12 and terminates near the tip 24. Bore 16 preferably has a matching taper to that of the driver 12, with both converging in a distal direction, to enhance driver-to-bore (screw) contact and to promote easier removal of the driver 10 from the bore 16. Preferably, the driver 10 has a friction fit relative to the bore 16, with the driver 10 extending substantially the entire length of the bore 16 when inserted therein, as shown in FIG. 4. It is preferred to maximize the driver-to-screw contact to distribute the insertion forces and avoid shear failure. FIG. 5 shows an alternative embodiment of the present invention wherein the driver 110 and bore 116 have a generally square cross-sectional shape, but is otherwise the same invention as that shown in FIGS. 1-4, like elements being labeled by reference numbers increased by 100.

The manufacturing processes used to make the bore 16, 116 of the screw 12, 112 and the driver 10, 110, whether by machining or molding, inherently involve dimensional tolerances. As a consequence, the mating surface areas of the screw 12, 112 and driver 10, 110 vary over a range due to normal dimensional variation of each of these parts. In the case of mating tapered parts, such as a tapered driver 10 and tapered bore 16, several dimensions including those for taped angle and length, and cross-sectional geometry, each have this inherent variation due to manufacturing.

Tolerance stack up analyses can be used to give a theoretical depiction of how these tolerance variations can affect the relative surface-to-surface contact area. At one extreme, when an undersized driver 10 is mated with an oversized bore 16, the driver 10 reaches its maximum depth within the bore 16. At the other extreme, when an oversized driver 10 is inserted into an undersized bore 16, the driver 10 only inserts partially and establishes a ring or line of relative contact. Given manufacturing tolerances, it would be rare to achieve full surface-to-surface contact at the driver 10 and bore 16 interface both circumferentially and longitudinally.

In accordance with the present invention, driver-to-screw contact can be maximized through a heat treatment performed on the polymeric-based cannulated screw 12 after insertion of driver 10. More particularly, the heat treatment induces dimensional shrinkage of the screw 12 so that the screw 12 closely grips the driver 10, maximizing driver-to-screw contact. The heat treatment process can be either a one step or multi-step process depending on the mechanisms that are involved in the heat treatment. In general, the driver 10 is inserted into bore 16 of screw 12 and both are exposed to heating to a temperature that is above the glass transition temperature (preferably 5 to 15° C. above the glass transition temperature) and below the melting temperature of screw 12 for a period of time. The mechanisms that can be utilized to induce the dimensional shrinkage are: (1) relaxation of internal stresses, (which, for example, can be produced due to injection molding); or (2) crystallization of the polymer material from which the screw 12 is made.

Suitable materials from which the driver 10 may be formed are typically, but not limited to, medically approved metallic materials, such as, stainless steel, titanium alloys thereof or other medically approved materials that do not plastically deform at the temperatures used to heat treat the polymeric-based medical screw 12.

The screw 12 can be made of any biocompatible or absorbable polymer, copolymer, or blend, provided heat treatment results in dimensional changes either through relaxation and/or crystallization in the material. Suitable materials from which the screw 12 may be formed include biocompatible polymers selected from the group consisting of aliphatic polyesters, polyorthoesters, polyanhydrides, polycarbonates, polyurethanes, polyamides and polyalkylene oxides.

In the preferred embodiment, the screw 12 is made from aliphatic polymers and copolymer polyesters and blends thereof. The aliphatic polyesters are typically synthesized in a ring opening polymerization. The aliphatic polyesters are typically synthesized in a ring opening polymerization. Suitable monomers include but are not limited to lactic acid, lactide (including L-, D-, meso and D, L mixtures), glycolic acid, glycolide, $\epsilon$-caprolactone, p-dioxanone (1,4-dioxan-2-one), trimethylene carbonate (1,3-dioxan-2-one), $\delta$-valerolactone, $\beta$-butyrolactone, $\epsilon$-decalactone, 2,5-diketomorpholine, pivalolactone, $\alpha,\alpha$-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

The screw 12 of the present invention can also be formed from polymeric composite materials reinforced with absorbable or biocompatible glasses or ceramics including phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium. These reinforcements can be in the form of particles, whiskers, platelets, fibers and the like.

EXAMPLES

The invention is further illustrated by the following non-limiting examples.

Example 1

An 15/85 (vol/vol) blend of beta-tricalcium phosphate ($\beta$-TCP, sold by CAM Implants bv, Leiden, Netherlands) and poly(L-lactic acid) (PLA, sold by Purac Biochem, Gorinchem bv, Netherlands, with an Inherent Viscosity of 2.3 dl/g when measured in $CHCl_3$ at a temperature of 25° C. and a concentration of 0.1 gm/dl was compounded on a twin-screw extruder. Screws similar to the polymer-based medical screw sold under the tradename ABSOLUTE (Mitek Products, Norwood, Mass.) were formed on an injection molder (Model NN35MI Super Mirs 4000, Niigata Engineering Company, Ltd., Itaska, Ill.) from the $\beta$-TCP/PLA blend. The screws were approximately 25-mm in (length) and 7-mm in (diameter). Differential scanning calorimetry (Model 2920, TA Instruments, New Castle, Del.) was performed on the unannealed screws to determine the percent crystallinity of the polymer. The polymer was amorphous.

Example 2

Ten screws from Example 1 were placed onto stainless steel drivers obtained from Mitek Norwood, Mass. and were annealed (Model AGC-3366 MP2 inert gas oven with PROSTAR controller, Blue M a unit of General Signal, Nanuet, N.Y.) in a nitrogen environment. The annealing cycle was: room temperature to 70° C. at a heating rate of 1° C./min, hold at 70° C. for 4 hrs, and cool to room temperature at ~1° C./min. Differential scanning calorimetry, as discussed in Example 1, was performed on the screws annealed to determine the percent crystallinity of the polymer. As in Example 1, the polymer was amorphous.

Example 3

Sixteen screws from Example 1 were placed onto stainless steel drivers and annealed as discussed in Example 2, but under a modified annealing cycle. For these screws, the modified annealing cycle was: room temperature to 70° C. at a heating rate of 1° C./min, hold at 70° C. for 4 hrs, heat to 100° C. at a heating rate of 1° C./min, hold at 100° C. for 8 hours, and cool to room temperature at ~1° C./min. Differential scanning calorimetry, as discussed in Example 1, was performed on these screws annealed with the modified cycle to determine the percent crystallinity of the polymer. In this case, the screws showed a crystallinity of 48 percent.

Testing of Examples 1, 2 and 3

Torque to strippage tests were performed on screws from Examples 1 through 3. Different screw and driver combinations/configurations were tested to determine the factors resulting in torque strippage improvement. These configurations are summarized in Table 1 and identified by sample set ID letters A-F. Screws from Example 1 (sample set F) were loaded onto randomly picked drivers. Screws from Example 2 were tested on the drivers on which they were annealed in two configurations: a screw and driver combination was either tested as taken from the annealing oven (sample set D), or removed from and then reloaded on to the same driver in its previous orientation (sample set E). Screws from Example 3 were tested in three configurations: on the drivers on which they were annealed, either as taken from the annealing oven (sample set B), or first removed from and then reloaded on to the same driver (sample set A), or removed from the annealing driver and loaded onto another, randomly picked driver (sample set C).

Torque testing of the foregoing configurations was performed using one-inch blocks of acetal resin, sold under the tradename DELRIN by E.I. du Pont de Nemours and Company, Wilmington, Del. The DELRIN blocks were drilled with a 5 mm pilot hole and tapped with a 7 mm tap. The screws identified in Table 1 were inserted into the tapped hole until strippage occurred at the driver-screw interface. The DELRIN block was secured to the base of the mechanical testing machine (MTS, 858 Mini Bionix with the following software: TestWare-SX version 4.0C and TestStar version 4.0D, MTS Systems Corporation, Eden Prarie, Minn.) while the proximal end of the driver was attached to the torque load cell with a set screw. Each screw was torqued at a rate of 10 deg/sec. The average torque at failure is shown in Table 2.

Torque tests were performed comparing specific sample sets to determine whether or not a statistical difference was observed at a confidence level greater than or equal to 95%.

The tests show that both heat treatment methods of Examples 2 and 3 resulted in statistical improvements in the torque to failure values compared to the unannealed screws (i.e., the failure torque of configurations A, B, D and E are statistically different than configuration F), but only when testing was performed using the same driver used during annealing. These results indicate that the process of crystallization in and of itself does not improve the torque to failure, in that the crystallized screws were statistically the same as the unannealed screws when removed from the driver after annealing and tested to torque failure using randomly chosen drivers (i.e., sample sets C and F are statistically the same). However, if the screw was removed and reloaded on the same driver with the same orientation as when annealing took place, the improvement in torque to failure values is maintained. The important factor in improving torque to failure is increasing the surface-to-surface contact area between the screw and the driver. This can be accomplished both through stress relaxation (e.g. 70° C. treatment of Example 2) which is applicable to both amorphous and crystallizable polymers and to a greater degree through crystallization (e.g., the 100° C. treatment of Example 3).

TABLE 1

Testing configurations between annealed and unannealed (as-molded) screws and drivers.

| Sample Set ID | Annealing Conditions [T(° C.)/t(hrs.)] | Screw-Driver Configuration |
|---|---|---|
| A | 100/8 | Removed & reloaded onto same driver |
| B | 100/8 | Left on annealing driver |
| C | 100/8 | Removed & reloaded onto random driver |
| D | 70/4 | Left on annealing driver |
| E | 70/4 | Removed & reloaded onto same driver |
| F | As-molded | Loaded onto random driver |

TABLE 2

Torque to failure testing results and statistics for annealed and unannealed (as-molded) screws

| Sample Set ID | Average Torque (in-lb) | Standard Deviation (in-lb) | Sample Set Size |
|---|---|---|---|
| A | 93.9 | 15.2 | 6 |
| B | 93.6 | 7.9 | 5 |
| C | 61.0 | 5.1 | 5 |
| D | 68.4 | 8.2 | 6 |
| E | 71.5 | 13.3 | 4 |
| F | 60.2 | 7.1 | 5 |

It will understood by those of skill in the art that numerous and various modifications can be made without departing from the spirit of the present invention and that the embodiments of the present invention described herein are illustrative only and are not intended to limit the scope of the present invention.

We claim:

1. A medical screw and driver system, comprising:
an elongated polymer screw having external threads and an internal bore extending through said screw along at least a portion of the length of said screw, said screw being formed from a biocompatible material and at least partially formed from a bioabsorbable material that is shrinkable upon heating, and said bore having an inner surface that is formed of said bioabsorbable material; and
an elongated driver having a non-circular cross-sectional shape approximating the cross-sectional shape of said bore, said driver being insertable into said bore, wherein said inner surface of said bore has been shrunken against said driver and conformed thereto upon heating said screw, thus achieving a closely mating shrink-fit of said bore relative to said driver such that said driver is matingly received within said bore to transfer rotational motion of said driver to said screw.

2. The system of claim 1, wherein said driver and said bore have a mating taper, each exhibiting a diminishing cross-sectional area in the direction of insertion of said driver into said cannula.

3. The system of claim 1, wherein said shrinkage is due to crystallization of said bioabsorbable material.

4. The system of claim 1, wherein said shrinkage is due to stress relaxation of said bioabsorbable material.

5. The system of claim 1, wherein said bioabsorbable material is selected from the group consisting of aliphatic polyesters, polyorthoesters, polyanhydrides, polycarbonates, polyurethanes, polyamides, and polyalkylene oxides.

6. The system of claim 5, wherein said screw has an additive to the composition thereof selected from the group consisting of bioabsorbable glass, bioabsorbable ceramic, biocompatible glass and biocompatible ceramic.

7. The system of claim 1, where said screw is composed of a 15/85 (vol/vol) blend of TCP/PLA.

8. The system of claim 1, wherein said screw is an orthopedic screw.

9. The system of claim 1, wherein said shrink-fit causes said bore to be in substantially continuous contact with said driver along the length of said bore.

10. The system of claim 9, wherein said shrink fit causes said bore to be in substantially continuous contact with said driver about the circumferential periphery of said bore.

11. The system of claim 1, wherein said driver is made of a material that does not plastically deform in response to the heating of said bioabsorbable material of said screw.

12. A medical screw and driver system, comprising:
an elongated polymer screw having external threads and an internal bore extending through said screw along at least a portion of the length of said screw, said screw being formed from a biocompatible material and at least partially formed from a bioabsorbable material that is shrinkable upon heating; and
an elongated driver having a non-circular cross-sectional shape approximating the cross-sectional shape of said bore, said driver being insertable into said bore, said screw and said bore having been shrunken and conformed to said driver by heating said screw so as to achieve a closely mating shrink-fit of said bore relative to said driver such that said driver is matingly received within said bore to transfer rotational motion of said driver to said screw and is withdrawn from and inserted into said bore without making further changes to said bore.

13. The system of claim 12, wherein said driver and said bore have a mating taper, each exhibiting a diminishing cross-sectional area in the direction of insertion of said driver into said cannula.

14. The system of claim 12, wherein said shrinkage is due to crystallization of said bioabsorbable material.

15. The system of claim 12, wherein said shrinkage is due to stress relaxation of said bioabsorbable material.

16. The system of claim 12, wherein said bioabsorbable material is selected from the group consisting of aliphatic polyesters, polyorthoesters, polyanhydrides, polycarbonates, polyurethanes, polyamides, and polyalkylene oxides.

17. The system of claim 16, wherein said screw has an additive to the composition thereof selected from the group consisting of bioabsorbable glass, bioabsorbable ceramic, biocompatible glass and biocompatible ceramic.

18. The system of claim 12, where said screw is composed of a 15/85 (vol/vol) blend of TCP/PLA.

19. The system of claim 12, wherein said screw is an orthopedic screw.

20. The system of claim 12, wherein said shrink-fit causes said bore to be in substantially continuous contact with said driver along the length of said bore.

21. The system of claim 20, wherein said shrink fit causes said bore to be in substantially continuous contact with said driver about the circumferential periphery of said bore.

22. The system of claim 12, wherein said driver is made of a material that does not plastically deform in response to the heating of said bioabsorbable material of said screw.

* * * * *